(12) United States Patent
Braun

(10) Patent No.: US 6,234,796 B1
(45) Date of Patent: May 22, 2001

(54) DENTAL ROOT CANAL TREATMENT

(75) Inventor: Günter Braun, Holzkirchen (DE)

(73) Assignee: VDW GmbH, Munich (DE)

( * ) Notice: Subject to any disclaimer, the term of this patent is extended or adjusted under 35 U.S.C. 154(b) by 0 days.

(21) Appl. No.: 09/497,759

(22) Filed: Feb. 4, 2000

Related U.S. Application Data

(63) Continuation-in-part of application No. PCT/EP99/03773, filed on May 31, 1999.

(30) Foreign Application Priority Data

Jun. 5, 1998 (DE) .............................................. 198 25 299

(51) Int. Cl.⁷ ...................................................... A61C 5/02
(52) U.S. Cl. ............................................ 433/102; 433/224
(58) Field of Search ...................................... 433/102, 224

(56) References Cited

U.S. PATENT DOCUMENTS 5,775,902 * 7/1998 Matsutani et al. .................... 433/102
5,868,570 * 2/1999 Hickok et al. ........................ 433/102

FOREIGN PATENT DOCUMENTS

| 4241921 | * | 4/1995 | (DE) . |
| 388675 | * | 3/1990 | (EP) . |
| 9622060 | * | 7/1996 | (WO) . |
| 9825536 | * | 6/1998 | (WO) . |

* cited by examiner

*Primary Examiner*—John J. Wilson
(74) *Attorney, Agent, or Firm*—Nixon Peabody LLP; David S. Safran

(57) ABSTRACT

A dental root canal instrument with a head part and an instrument part connected thereto. To lengthen the useful lifetime of the instrument, the instrument part has a coating of a wear-resistant material over at least a part of its length. The coating preferably has a certain color which is characteristic of the respective type of dental root canal instrument.

8 Claims, 1 Drawing Sheet

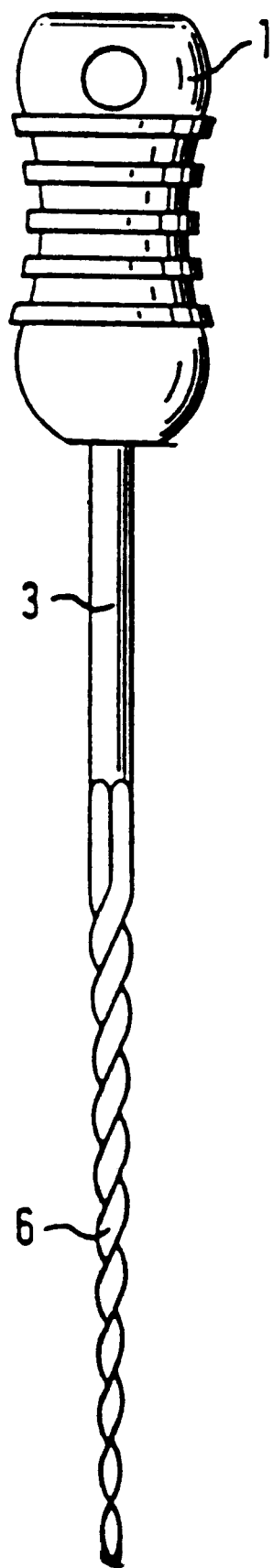

DENTAL ROOT CANAL TREATMENT

CROSS REFERENCE TO RELATED APPLICATION

This application is a continuation-in-part of commonly owned, co-pending International Patent Application No. PCT/EP99/03773 filed on May 31, 1999 which designated the United States.

BACKGROUND OF THE INVENTION

This invention concerns a dental root canal instrument with a head part and an instrument part connected thereto.

DESCRIPTION OF RELATED ART

Dental root canal instruments of the type to which the invention is directed are known and are used in particular for treating dental root canals. To do so, the instrument part is preferably designed as a cutting instrument with which a dental root canal can be reamed out.

Dental root canal instruments of the type described above are exposed to great wear, so they usually have only a short lifetime.

SUMMARY OF THE INVENTION

Therefore, a primary object of the present invention is to create a dental root canal instrument with a longer lifetime.

This object is achieved according to this invention by coating the instrument part with a wear-resistant material over at least part of its length.

Especially preferred embodiments of and improvements upon the dental root canal instrument according to this invention include the thickness of the coating being in the range of 0.1 to 5 μm, and the wear-resistant material having a certain color which is characteristic of the respective instrument, being physiologically safe, stable at temperatures up to 200° C. without the flexibility and elasticity of the instrument part being impaired.

An especially preferred embodiment of this invention is described in greater detail below with reference to the accompanying drawings.

BRIEF DESCRIPTION OF THE DRAWINGS

The sole FIGURE of the drawings shows a root canal treatment instrument in accordance with the present invention.

DETAILED DESCRIPTION OF THE INVENTION

As shown in the FIGURE, a dental root canal instrument usually includes a head part 3 with which the instrument can be mounted on a hand-guided drive part 1, and a working part 6 connected to it that is equipped with one or more cutting edges for reaming out dental root canals.

The working part 6 is coated with a wear-resistant material over at least a portion of its length, the layer thickness preferably being in the range of 0.1 to 5 μm.

The wear-resistant material should be physiologically safe and sterilizable, and therefore, should be stable at temperatures up to 200° C. It should not have any negative reactions with conventional disinfectants.

The wear-resistant material should also be so flexible that the flexibility and elasticity of the instrument part are not impaired. Furthermore, the wear-resistant material should not have any negative effect on the mechanical properties of the base material of which the instrument part is made.

In addition, the material of the coating should be selected and the coating applied in such a way that the coating will not crack or flake off due to bending of the instrument part during use.

The wear-resistant material is harder than the base material of which the instrument part is made, and it makes the blades of the instrument part more resistant to wear in root canal treatments, which lengthens the service life of an instrument and thus prolongs its lifetime.

The base material may be a high-grade stainless steel, a nickel-titanium alloy or a special alloy having good properties for use as a root canal instrument accordingly.

The wear-resistant material, which should be harder than the base material, is in particular carbon or a carbon compound, titanium or titanium nitrite or compounds thereof, silicone or a silicone compound, titanium aluminum nitrite or a compound thereof, silicon or a compound thereof, amorphous boron carbide (ABC layer) or chromium or a compound thereof.

However, essentially all material having properties such that the wear-resistance of the base material or the use conditions of the instruments coated accordingly are improved are suitable.

The coating preferably has a certain color to differentiate the coated instrument from another instrument with a coating of another color or an instrument without a coating, where the color of the coating is used to distinguish one instrument from similar instruments having other properties. The color is thus used to characterize instruments with the same properties, which is especially advantageous in the case of dental root canal instruments, because other identification options are possible only to a very limited extent due to the small size of the instruments.

The color identification of the coating also has the advantage that the user can recognize that the instrument must be replaced when the coating has worn off in the area of the instrument part, in particular the cutting edges. A colored coating may also be used to different entire groups of instruments from others.

I claim:

1. A dental root canal instrument comprising a head part and a working part of a first color which is connected thereto, wherein the working part is coated with a wear-resistant material over at least part of its length, and wherein said wear-resistant material is a second color which is different from the first color of said working part as a means for indicating to a user when said instrument must be replaced by a change in color associated with wearing off of the coating to reveal the first color of the working.

2. A dental root canal instrument according to claim 1, wherein that the coating has a thickness in a range of 0.1 to 5 μm.

3. A dental root canal instrument according to claim 1, wherein that the wear-resistant material has a color which is characteristic of a respective type of instrument.

4. A dental root canal instrument according to claim 1, wherein the wear-resistant material is physiologically safe.

5. A dental root canal instrument according to claim 1, wherein the wear-resistant material is stable at temperatures up to 200° C. for enabling sterilization thereof, and nonreactive with disinfectants from a standpoint of negative effects.

6. A dental root canal instrument according to claim 1, wherein the wear-resistant material has flexibility and elasticity at least as great as that of the working part so as not to adversely affect the flexibility and elasticity of the working part.

7. A dental root canal instrument according to claim 1, wherein the wear-resistant material has mechanical properties which are compatible with the mechanical properties of the base material of which the working part.

8. A dental root canal instrument according to claim 1, wherein the wear-resistant material is selected from the group of materials consisting of carbon and carbon compounds, titanium and titanium nitrite as well as compounds thereof, silicone and silicone compounds, titanium aluminum nitrite and compounds thereof, silicon and compounds thereof, amorphous boron carbide and chromium and compounds thereof.

\* \* \* \* \*